United States Patent
Katsumata

(10) Patent No.: US 11,090,021 B2
(45) Date of Patent: Aug. 17, 2021

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventor: Shinya Katsumata, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 16 days.

(21) Appl. No.: 16/705,678

(22) Filed: Dec. 6, 2019

(65) Prior Publication Data
US 2020/0178922 A1    Jun. 11, 2020

(30) Foreign Application Priority Data

Dec. 11, 2018 (JP) .............................. JP2018-231546

(51) Int. Cl.
*A61B 6/00*    (2006.01)
*G01N 23/04*    (2018.01)

(52) U.S. Cl.
CPC .............. *A61B 6/58* (2013.01); *A61B 6/483* (2013.01); *A61B 6/505* (2013.01); *G01N 23/04* (2013.01); *G01N 2223/401* (2013.01)

(58) Field of Classification Search
CPC ........... A61B 6/58; A61B 6/483; A61B 6/505; G01N 23/04
See application file for complete search history.

(56) References Cited

U.S. PATENT DOCUMENTS

| 9,569,829 B2 | 2/2017 | Ohguri et al. |
| 2003/0165216 A1* | 9/2003 | Walker .................. A61B 6/544 378/108 |
| 2006/0269114 A1* | 11/2006 | Metz ..................... G06T 11/008 382/131 |
| 2008/0292217 A1* | 11/2008 | Claus .................... G06T 11/006 382/304 |
| 2016/0235384 A1 | 8/2016 | Enomoto et al. |
| 2017/0360391 A1 | 12/2017 | Kawamura |
| 2018/0232872 A1 | 8/2018 | Katsumata |

FOREIGN PATENT DOCUMENTS

| JP | 2003209746 A | 7/2003 |
| JP | 5602014 B2 | 10/2014 |
| JP | 2018153605 A | 10/2018 |

OTHER PUBLICATIONS

Extended European Search Report issued by the European Patent Office dated May 11, 2020 in corresponding European Patent Application No. 19211930.3.

* cited by examiner

*Primary Examiner* — Hugh Maupin
(74) *Attorney, Agent, or Firm* — Carter, DeLuca & Farrell LLP

(57) ABSTRACT

An image processing apparatus for processing a radiation image output from a radiation detection unit including a plurality of pixels, comprises: an imaging protocol obtaining unit configured to obtain an imaging protocol for imaging a subject; and a dose obtaining unit configured to obtain dose information of radiation based on a feature amount of the radiation image and information obtained from the imaging protocol.

19 Claims, 5 Drawing Sheets

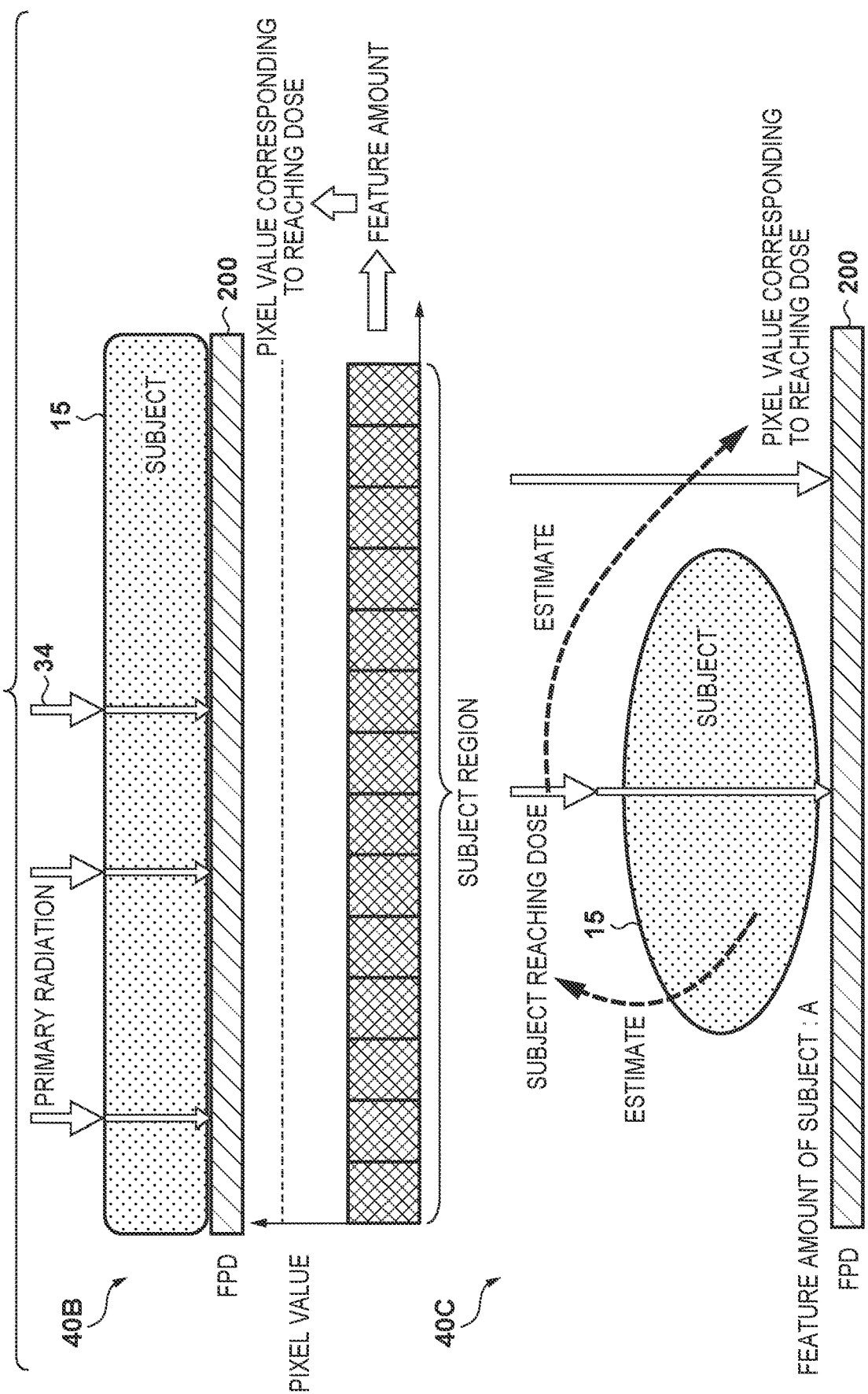

IMAGE PROCESSING APPARATUS, IMAGE PROCESSING METHOD, AND STORAGE MEDIUM

BACKGROUND OF THE INVENTION

Field of the Invention

The present invention relates to an image processing apparatus, an image processing method, and a storage medium.

Description of the Related Art

In recent years, a radiation imaging apparatus using a device called a flat panel detector (to be referred to as an "FPD" hereinafter) in which a number of semiconductor elements each for converting radiation into an electrical signal are disposed in a two-dimensional matrix has become widespread.

When imaging a subject using the radiation imaging apparatus, radiation entering the FPD is mainly separated into two kinds of components including primary radiation that travels in a straight line from a radiation source to reach the FPD and secondary radiation (to be referred to as "scattered radiation" hereinafter) that reaches the FPD after the direction of radiation changes in the subject.

Among various methods (to be referred to as "scattered radiation reducing processes" hereinafter) of reducing scattered radiation by obtaining a scattered radiation component from a radiation image captured by the radiation imaging apparatus, and subtracting the obtained scattered radiation component from the radiation image, there is a method using the dose (to be referred to as the "reaching dose" hereinafter) of radiation having reached the FPD.

To obtain the reaching dose, there are, for example, a method of obtaining dose information by installing a dose area product meter in the radiation imaging apparatus, a method of obtaining imaging information such as an SID (Source to Image Distance) and dose information based on a tube current and an irradiation time from a radiation generation unit by information communication, and a method of obtaining the reaching dose using the pixel value of a radiation image. If the reaching dose is obtained from the pixel value of a radiation image, a pixel value in a region (to be referred to as a "direct radiation region" hereinafter) where radiation directly reaches a radiation detection unit from a radiation generation unit is proportional to the reaching dose, and it is thus possible to obtain the dose from the pixel value in the direct radiation region.

Japanese Patent Laid-Open No. 2003-209746 discloses a method of correcting, using the image lag component of an image additionally obtained from an FPD after obtaining a radiation image, a pixel value from which an original pixel value is obtained from an image lag.

However, in the conventional technique, since it is impossible to estimate a reaching dose when it is impossible to obtain imaging information by information communication due to the influence of a communication environment, when a pixel value in a direct radiation region is saturated, or when there is no direct radiation region, it may be impossible to execute a scattered radiation obtaining process.

The present invention has been made in consideration of the above problem, and provides an image processing technique capable of obtaining a reaching dose or a pixel value corresponding to the reaching dose based on a captured radiation image and an imaging protocol.

SUMMARY OF THE INVENTION

According to one aspect of the present invention, there is provided an image processing apparatus for processing a radiation image output from a radiation detection unit including a plurality of pixels, comprising: an imaging protocol obtaining unit configured to obtain an imaging protocol for imaging a subject; and a dose obtaining unit configured to obtain dose information of radiation based on a feature amount of the radiation image and information obtained from the imaging protocol.

According to another aspect of the present invention, there is provided an image processing method of processing a radiation image output from a radiation detection unit including a plurality of pixels, comprising: obtaining an imaging protocol for imaging a subject; and obtaining dose information of radiation based on a feature amount of the radiation image and information obtained from the imaging protocol.

According to the present invention, it is possible to obtain a reaching dose or a pixel value corresponding to the reaching dose based on a captured radiation image and an imaging protocol.

Further features of the present invention will become apparent from the following description of exemplary embodiments (with reference to the attached drawings).

BRIEF DESCRIPTION OF THE DRAWINGS

FIG. 4B indicates 40B being a view schematically showing a radiation irradiation state in a region (subject region) other than a direct radiation region, and indicates 40C being a view schematically showing a subject reaching dose and a pixel value corresponding to the reaching dose.

DESCRIPTION OF THE EMBODIMENTS

Figure 1:
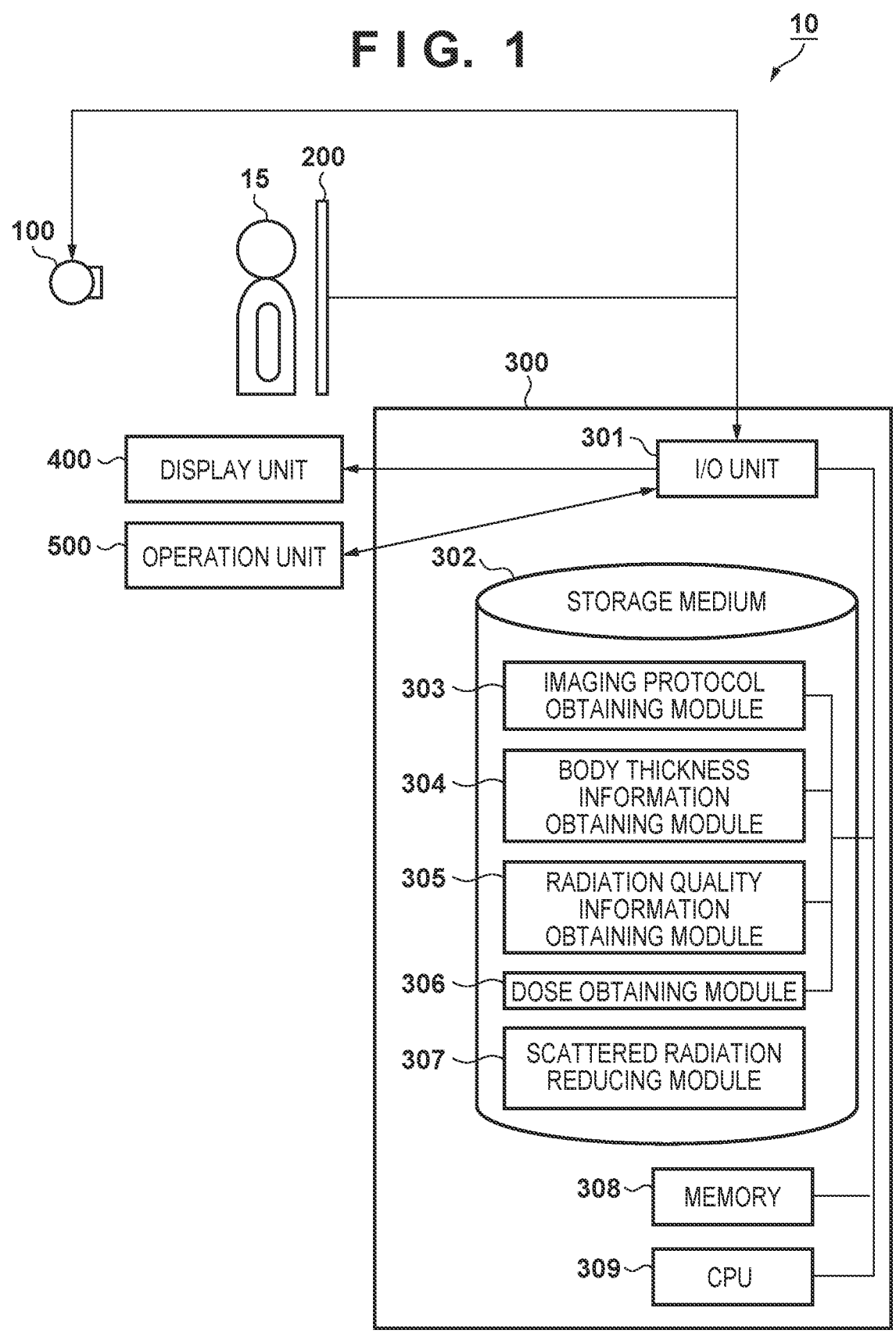
FIG. 1 is a view showing an example of the arrangement of a radiation imaging apparatus according to an embodiment.

An embodiment of the present invention will be described in detail below with reference to the accompanying drawings. Note that the following embodiment does not limit the invention according to the scope of the appended claims. Although a plurality of features are described in the embodiment, not all the features are essential to the invention and the plurality of features may be arbitrarily combined. Throughout the accompanying drawings, the same reference numerals denote the same or similar components and a repetitive description thereof will be omitted. Each of the embodiments of the present invention described below can be implemented solely or as a combination of a plurality of the embodiments or features thereof where necessary or where the combination of elements or features from individual embodiments in a single embodiment is beneficial.

FIG. 1 is a view showing an example of the arrangement of a radiation imaging apparatus 10 according to the embodiment. First, an FPD 200 (radiation detection unit) arranged on an extension line of a subject 15 is irradiated with radiation from a radiation tube 100. After the FPD 200 is irradiated with radiation, it converts radiation into a captured image, and transmits the converted captured image to an I/O unit 301 of an image processing unit 300. At this time, the image processing unit 300 that processes the captured image (to also be referred to as a radiation image hereinafter) output from the FPD 200 (radiation detection unit) including a plurality of pixels can obtain, from the radiation tube 100, an imaging protocol (imaging information) concerning imaging conditions such as a dose and a tube voltage at the time of image capturing and the like. An operation unit 500 is used to, for example, operate the image processing unit 300 and input the captured image.

The I/O unit 301 (input/output unit) obtains the captured image transmitted from the FPD 200 and the imaging protocol (imaging information) transmitted from the radiation tube 100, and saves them in a storage medium 302. The storage medium 302 saves, as functional components for executing various processes by executing an image processing program, an imaging protocol obtaining module 303 that obtains the imaging protocol of the radiation tube 100, a body thickness information obtaining module 304 that obtains the body thickness information of the subject 15, a radiation quality information obtaining module 305 that obtains the radiation quality information of radiation emitted from the radiation tube 100, a dose obtaining module 306 that obtains the reaching dose of radiation that directly reaches the FPD 200 (radiation detection unit) from the radiation tube 100 (radiation generation unit), and a scattered radiation reducing module 307 that reduces scattered radiation based on the reaching dose.

Under the control of a CPU 309 functioning as a control unit, the respective function components (imaging protocol obtaining module 303, body thickness information obtaining module 304, radiation quality information obtaining module 305, dose obtaining module 306, and scattered radiation reducing module 307) can temporarily read out the imaging protocol (imaging information) and captured image saved in the storage medium 302 into a memory 308 functioning as a work area, and execute various calculation processes.

The CPU 309 (control unit) can perform display control for displaying the result of an image process on a display unit 400. Note that a calculation apparatus such as a GPU or a chip for an image process can be used instead of the CPU 309.

Figure 2:
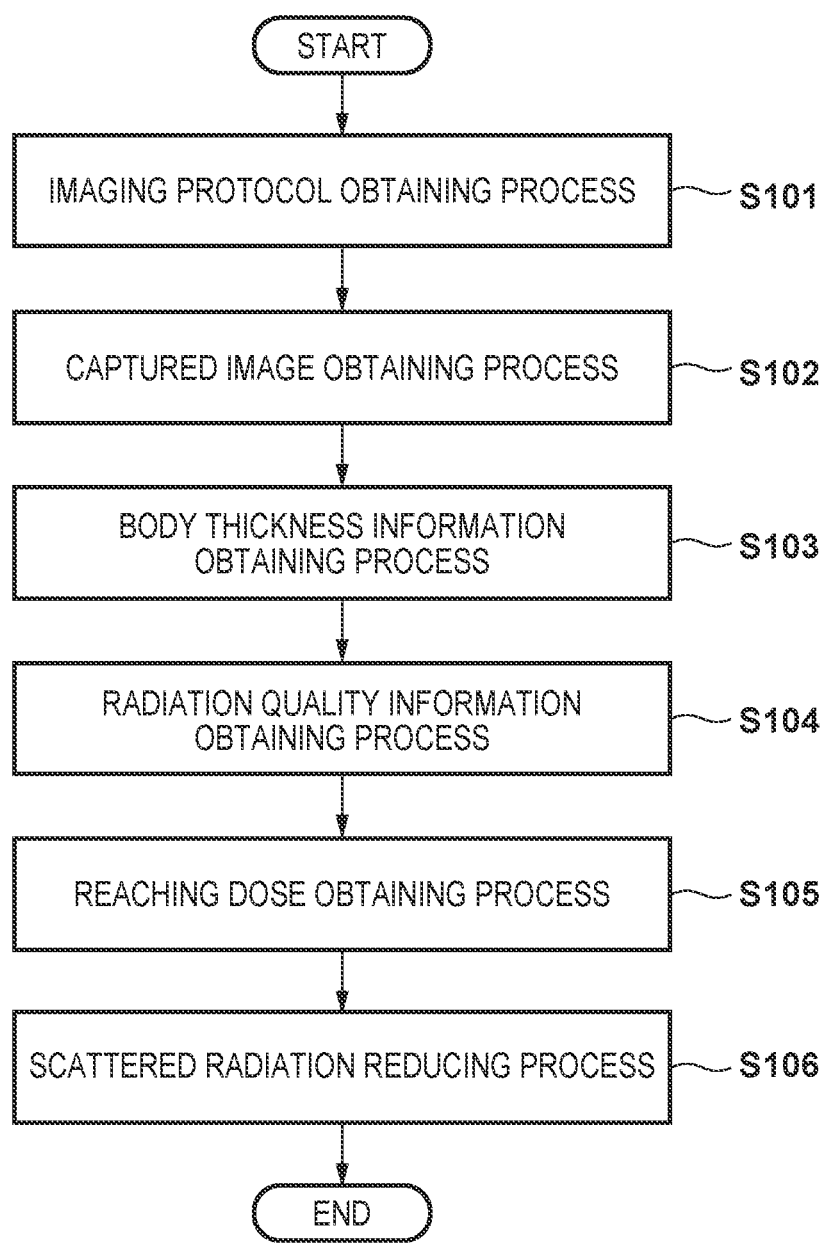
FIG. 2 is a flowchart for explaining the procedure of the schematic process of each functional component of an image processing unit according to the embodiment.

The procedure of the schematic process of each functional component of the image processing unit 300 will be described with reference to a flowchart shown in FIG. 2. In step S101, the imaging protocol obtaining module 303 performs an imaging protocol obtaining process to obtain an imaging protocol in radiation imaging. In step S102, a captured image obtaining process of obtaining a captured image (radiation image) from the FPD 200 is performed. In the captured image obtaining process, for example, the image processing unit 300 may obtain the captured image from the FPD 200 via the I/O unit 301 or obtain the captured image saved in the storage medium 302.

In step S103, the body thickness information obtaining module 304 performs a body thickness information obtaining process of obtaining the body thickness information of the subject 15 based on the imaging protocol obtained in the imaging protocol obtaining process in step S101. In step S104, the radiation quality information obtaining module 305 performs a radiation quality information obtaining process of obtaining the radiation quality information of emitted radiation based on the imaging protocol obtained in the imaging protocol obtaining process in step S101.

In step S105, the dose obtaining module 306 performs a reaching dose obtaining process to obtain, based on the captured image obtained in step S102, the body thickness information obtained in step S103, and the radiation quality information obtained in step S104, the reaching dose of radiation that directly reaches the FPD 200 (radiation detection unit) from the radiation tube 100 (radiation generation unit).

In step S106, the scattered radiation reducing module 307 performs a scattered radiation reducing process using the reaching dose obtained in the reaching dose obtaining process in step S105. The scattered radiation reducing module 307 performs a scattered radiation estimation process of estimating scattered radiation using the reaching dose, and performs, using a scattered radiation estimation image obtained in the scattered radiation estimation process, a scattered radiation reducing process of obtaining a scattered radiation reduction image by excluding the scattered radiation estimation image from the captured image.

[Imaging Protocol Obtaining Process: S101]

The process of the imaging protocol obtaining module 303 will be described as the process of the functional component of the image processing unit 300. The imaging protocol described here is imaging information for imaging a subject, and mainly represents, for example, imaging information set for each imaging technique such as front-of-chest imaging or side-of-abdomen imaging. The imaging protocol obtaining module 303 obtains the imaging protocol (imaging information) for imaging a subject. Contents of the set imaging information include, for example, an imaging portion and an imaging direction, information of the type of an additional filter and the tube voltage of the radiation tube 100 used by the imaging technique, image processing parameters such as the rotation angle of an image, or information of the energy spectral property of radiation. The imaging protocol can be preset for each imaging technique.

As a practical example of the imaging protocol obtaining process, the user selects the imaging protocol from the preset imaging protocols using the operation unit 500 in accordance with the imaging technique. After the imaging protocol is selected using the operation unit 500, the imaging protocol obtaining module 303 can obtain, for example, the imaging protocol selected from the plurality of imaging protocols stored in the storage medium 302. The obtaining source of the plurality of imaging protocols is not limited to the storage medium 302, and the imaging protocols can also be obtained from an external apparatus (server) via a network. If the image processing unit 300 is connected to the network via the I/O unit 301, the imaging protocol obtaining module 303 can obtain, from the server via the network, the information of the imaging technique selected by the user using the operation unit 500, and set the imaging protocol corresponding to the imaging technique.

[Captured Image Obtaining Process: S102]

The captured image obtaining process of obtaining a captured image will be described next. As an example of the method of obtaining a captured image, for example, the image processing unit 300 may obtain a captured image from the FPD 200 via the I/O unit 301 or obtain a captured image saved in the storage medium 302 or the memory 308. If a captured image is obtained by transfer from the FPD 200, when radiation emitted from the radiation tube 100 at the start of imaging is transmitted through the subject 15 to reach the FPD 200, the FPD 200 converts radiation into a captured image, and transfers the converted captured image to the image processing unit 300. The image processing unit 300 obtains the captured image transferred from the FPD 200 via the I/O unit 301.

[Body Thickness Information Obtaining Process: S103]

The process of the body thickness information obtaining module 304 will be described as the process of the functional component of the image processing unit 300. The body thickness information indicates the thickness of the subject 15 in a direction from the radiation tube 100 to the FPD 200. The body thickness information obtaining module 304 obtains the body thickness information of the subject 15 based on the imaging protocol (imaging information). The body thickness information obtaining module 304 performs a body thickness information obtaining process based on the imaging protocol obtained in the imaging protocol obtaining process (step S101). Body thickness information can be preset in the imaging protocol. The body thickness information obtaining module 304 obtains body thickness information associated with the imaging portion or imaging direction of the subject 15 included in the imaging protocol (imaging information).

As a practical method of the body thickness information obtaining process, if the information of the imaging protocol obtained in the imaging protocol obtaining process (step S101) includes body thickness information, the body thickness information obtaining module 304 obtains the body thickness information from the imaging protocol, and outputs the obtained body thickness information to the dose obtaining module 306.

Alternatively, the body thickness information obtaining module 304 specifies the imaging portion and the imaging direction included in the information of the imaging protocol obtained in step S101, and obtains the body thickness information corresponding to the specified imaging portion and imaging direction with reference to a body thickness information table 320. The body thickness information obtaining module 304 can output the obtained body thickness information to the dose obtaining module 306.

Figure 3:
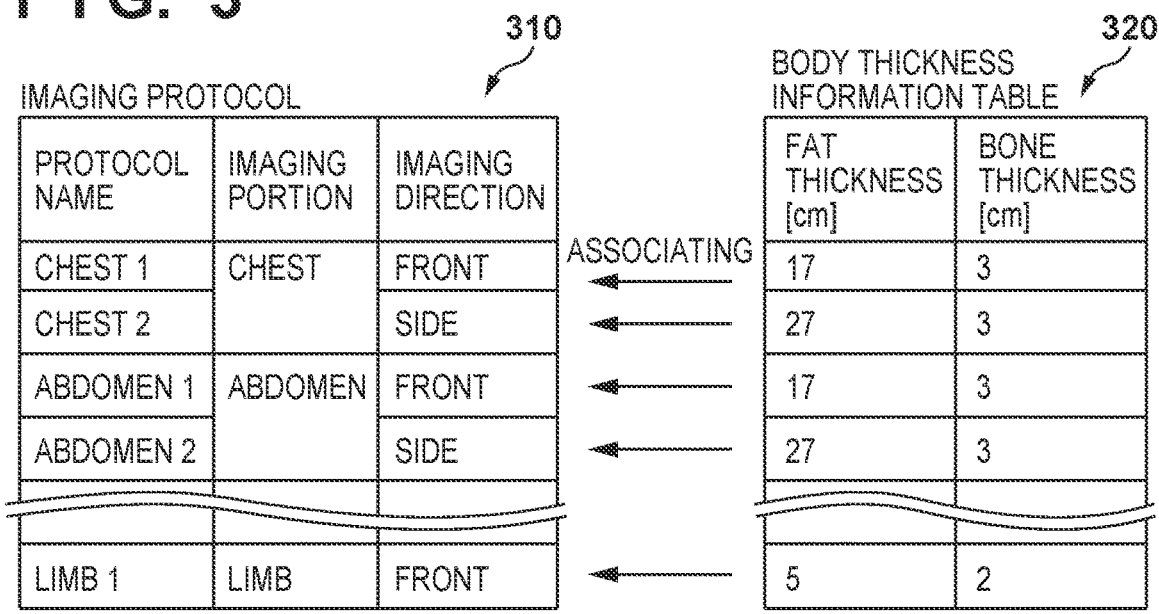
FIG. 3 is a view exemplifying the structure of a body thickness information table corresponding to an imaging protocol.

FIG. 3 is a view exemplifying the arrangement of the body thickness information table 320 corresponding to an imaging protocol 310. Body thickness information stored in the body thickness information table 320 indicates the thickness of the subject 15 in the direction from the radiation tube 100 to the FPD 200. As shown in FIG. 3, the body thickness information is finely divided for each tissue of the subject 15. For example, pieces of tissue body thickness information of respective tissues, such as a fat thickness and a bone thickness, can be stored in the body thickness information table 320.

As shown in FIG. 3, the body thickness information is stored in the body thickness information table 320 in correspondence with the imaging portion and the imaging direction included in the imaging protocol 310. If, for example, chest 1 is selected as an imaging protocol, the body thickness information obtaining module 304 obtains the body thickness information (for example, fat thickness: 17 cm, bone thickness: 3 cm, and the like) corresponding to the imaging portion and the imaging direction included in the imaging protocol (chest 1) with reference to the body thickness information table 320. In this case, the body thickness information obtaining module 304 obtains, as the body thickness information, the total of the pieces of tissue body thickness information of the respective tissues, and outputs the obtained body thickness information to the dose obtaining module 306. Note that the pieces of tissue body thickness information of the respective tissues, such as a fat thickness and a bone thickness shown in FIG. 3, are merely examples, and the present invention is not limited to them.

The body thickness information table 320 for associating the imaging protocol (imaging information) and the body thickness information (fat thickness, bone thickness, and the like) with each other can be stored in advance in, for example, the storage medium 302, and the body thickness information obtaining module 304 can obtain the body thickness information corresponding to the imaging portion and the imaging direction included in the imaging protocol from the body thickness information table 320 stored in the storage medium 302. The storage destination of the body thickness information table 320 is not limited to the storage medium 302, and the body thickness information table 320 can also be obtained from an external apparatus (server) via the network. If the image processing unit 300 is connected to the network via the I/O unit 301, the body thickness information obtaining module 304 can obtain the body thickness information corresponding to the imaging portion and the imaging direction from the body thickness information table 320 of the external apparatus (server) via the network.

[Radiation Quality Information Obtaining Process: S104]

The process of the radiation quality information obtaining module 305 will be described as the process of the functional component of the image processing unit 300. The radiation quality information obtaining module 305 performs a radiation quality information obtaining process of obtaining the radiation quality information of radiation based on the imaging protocol (imaging information) obtained in the imaging protocol obtaining process (step S101). It is possible to preset, as radiation quality information, information of the energy spectral property (to be referred to as the spectral property hereinafter) of radiation in the imaging protocol.

As a practical method of the radiation quality information obtaining process, if the information of the spectral property is included in the information of the imaging protocol obtained in the imaging protocol obtaining process (step S101), the radiation quality information obtaining module 305 obtains the information of the spectral property from the imaging protocol, and outputs the obtained information of the spectral property to the dose obtaining module 306.

It is possible to hold in advance the information of the spectral property as radiation quality information in the storage medium 302. For example, it is possible to divide the spectral property into bins of spectral units (energy component units of radiation), and store, in the storage medium 302, a table indicating a content for each spectral unit in radiation emitted from the radiation tube 100.

It is also possible to set, in the information of the imaging protocol, at least one of the information of the type of the additional filter and the tube voltage of the radiation tube 100, and the radiation quality information obtaining module 305 can obtain, as the radiation quality information of radiation, the information of the spectral property of radiation in radiation imaging obtained from the table of the preset spectral property, based on the tube voltage or the filter type included in the imaging protocol (imaging information) obtained in the imaging protocol obtaining process (step S101), and output the obtained information of the spectral property (the obtained radiation quality information of radiation) to the dose obtaining module 306.

The preset spectral property in the table is property information corresponding to a change in radiation quality of emitted radiation caused by the tube voltage or additional filter, and indicates the spectral property of radiation that reaches the FPD 200. The spectral property preset in the table can be obtained by, for example, a measurement device such as a spectral analyzer in an experiment. The spectral property may be set in the table based on information obtained by performing a statistical process of measurement information, such as the average value or the median value of pieces of measurement information obtained by performing measurement for the plurality of radiation tubes 100.

[Reaching Dose Obtaining Process: S105]

Figure 4A:
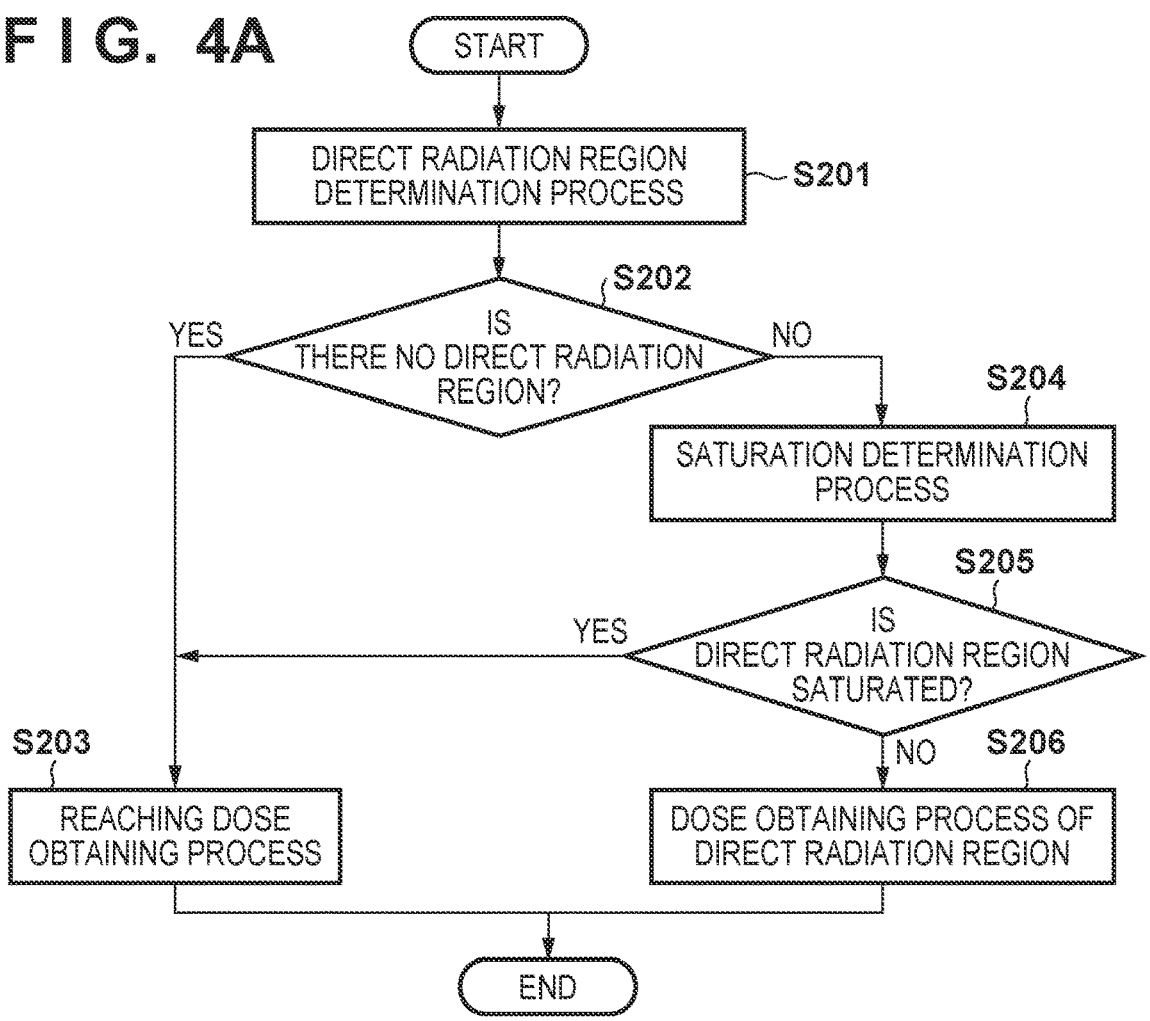
FIG. 4A is a flowchart for explaining the procedure of a reaching dose obtaining process.

The process of the dose obtaining module 306 will be described as the process of the functional component of the image processing unit 300. The dose obtaining module 306 performs a reaching dose obtaining process using at least one of the captured image obtained in the captured image obtaining process (step S102), the body thickness information obtained in the body thickness information obtaining process (step S103), and the radiation quality information obtaining process (step S104). FIG. 4A is a flowchart for explaining the procedure of the reaching dose obtaining process.

(Direct Radiation Region Determination Process: S201)

In step S201, the dose obtaining module 306 performs a direct radiation region determination process of determining, based on the pixel value of the captured image (radiation image), a direct radiation region where radiation directly reaches the FPD 200 (radiation detection unit) from the radiation tube 100 (radiation generation unit) and a region (non-direct radiation region) other than the direct radiation region. In the direct radiation region determination process, the dose obtaining module 306 can determine a pixel exceeding a threshold as a direct radiation region based on the pixel value of the captured image (radiation image) by setting, as the threshold, a value of a fixed ratio to the upper level of the pixel value in the captured image. Alternatively, the pixel values may be separated into the direct radiation region and the region other than the direct radiation region based on a histogram of the pixel values using the k-means method.

The dose obtaining module 306 can obtain, based on the determination result, direct radiation region information (direct radiation region map) indicating the distribution of the direct radiation region. The direct radiation region information (direct radiation region map) can be implemented by making it possible to distinguish the information as an image in which pixels indicating the direct radiation region have "1" and the remaining region has "0". The image in which the pixels indicating the direct radiation region have "1" and the remaining region has "0" is obtained as the direct radiation region map, and the captured image can be divided into the direct radiation region and the remaining region by the direct radiation region determination process.

In step S202, if, as a result of the direct radiation region determination process, it is determined that there is no direct radiation region (YES in step S202), the dose obtaining module 306 advances the process to step S203 to perform a reaching dose obtaining process. The reaching dose obtaining process (step S203) will be described later. On the other hand, if it is determined in step S202 that there is the direct radiation region (NO in step S202), the dose obtaining module 306 advances the process to step S204 to perform a saturation determination process of determining whether a pixel in the direct radiation region is saturated.

(Saturation Determination Process: S204)

In step S204, the dose obtaining module 306 performs the saturation determination process of determining whether the pixel of the FPD 200 in the direct radiation region is saturated. The dose obtaining module 306 compares the preset theoretical value or actual measured value (the theoretical value or actual measured value will be referred to as "the reference value of the saturated pixel value" hereinafter) of the saturated pixel value in the FPD 200 with the pixel value in the direct radiation region. If the pixel value in the direct radiation region is equal to or larger than the reference value, the dose obtaining module 306 determines that the pixel value in the direct radiation region is saturated; otherwise, the dose obtaining module 306 determines that the pixel value in the direct radiation region is not saturated.

If, as a result of the saturation determination process, it is determined in step S205 that the pixel in the direct radiation region is not saturated (NO in step S205), the dose obtaining module 306 advances the process to step S206 to perform the dose obtaining process of the direct radiation region.

(Dose Obtaining Process of Direct Radiation Region: S206)

In step S206, if the pixel value in the direct radiation region is not saturated, the dose obtaining module 306 obtains, as dose information, a reaching dose of radiation having reached the FPD 200 (radiation detection unit) or a pixel value corresponding to the reaching dose using information obtained by performing a statistical process of the pixel value of the radiation image. The dose obtaining module 306 obtains, from the captured image obtained in step S102, the feature amount of the image (pixel group) corresponding to the direct radiation region obtained in the direct radiation region determination process (step S201), thereby obtaining the pixel value corresponding to the reaching dose. As the feature amount, for example, information (pixel value information such as the maximum value, the average value, or the median value) obtained by performing a statistical process of the pixel value of the radiation image in the direct radiation region can be used. Furthermore, with respect to conversion between the pixel value and the dose, for example, if the correspondence between the dose and the pixel value is obtained in advance by a dosimeter or the like, and the pixel value is converted into the dose based on the correspondence, it is possible to obtain the reaching dose in the direct radiation region. However, if the reaching dose is used for an image process or the like, it is possible to use the pixel value intact without converting the pixel value into the dose.

On the other hand, if, as a result of the saturation determination process, it is determined in step S205 that the pixel in the direct radiation region is saturated (YES in step S205), the dose obtaining module 306 advances the process to step S203 to perform a reaching dose obtaining process.

(Reaching Dose Obtaining Process: S203)

In step S203, the dose obtaining module 306 obtains dose information of radiation based on the feature amount of the captured image (radiation image) and the information obtained from the imaging protocol. In this example, the information obtained from the imaging protocol includes, for example, the body thickness information of the subject 15 and the radiation quality information of radiation, both of which have been obtained from the captured image (radiation image). Note that the body thickness information of the subject 15 and the radiation quality information of radiation are merely examples of the information obtained from the imaging protocol, and the present invention is not limited to them. The dose obtaining module 306 obtains, as the dose information, the reaching dose of radiation having reached the FPD 200 (radiation detection unit) and the pixel value corresponding to the reaching dose. If there is no direct radiation region or if the pixel value in the direct radiation region is saturated, the dose obtaining module 306 obtains, as the dose information, the reaching dose of radiation having reached the FPD 200 (radiation detection unit) and the pixel value corresponding to the reaching dose based on the feature amount of the captured image (radiation image) and an attenuation property obtained based on the imaging protocol (imaging information).

At this time, the dose obtaining module 306 obtains, as the attenuation property, an attenuation rate ($R_1 \cdot R_2$) of the subject 15 and an attenuation rate $R_{Air}$ of air based on the body thickness information and the radiation quality information, both of which have been obtained based on the imaging protocol (imaging information). The dose obtaining module 306 performs a reaching dose obtaining process based on equations (1) to (3) below to obtain the pixel value corresponding to the reaching dose, and performs a dose conversion process of converting the pixel value corresponding to the reaching dose into a dose. A method of converting the pixel value into the dose is the same as that in the conversion process in step S206. That is, with respect to conversion between the pixel value and the dose, for example, if the correspondence between the dose and the pixel value is obtained in advance by a dosimeter or the like, and the pixel value is converted into the dose based on the correspondence, it is possible to obtain the dose corresponding to the pixel value. It is also possible to obtain the pixel value corresponding to the dose based on the correspondence.

40B and 40C of FIG. 4B are views schematically showing an overview of a process of obtaining (estimating) the pixel value corresponding to the reaching dose. 40B of FIG. 4B is a view schematically showing a radiation irradiation state in the region (subject region) other than the direct radiation region. Referring to 40B of FIG. 4B, radiation 34 emitted from the radiation tube 100 is transmitted through the subject 15 to reach the FPD 200. A pixel value based on radiation transmitted through the subject 15 is smaller than a pixel value (a pixel value corresponding to a reaching dose) based on primary radiation that travels in a straight line from the radiation tube 100 to reach the FPD 200.

40C of FIG. 4B is a view schematically showing a pixel value (a pixel value corresponding to a reaching dose) based on the dose (subject reaching dose) of radiation having reached the subject 15 and the dose of primary radiation having reached the FPD 200. Since radiation having reached the subject 15 attenuates in the subject 15, the dose of radiation that is transmitted through the subject 15 to reach the FPD 200 tends to decrease, as compared with the subject reaching dose.

In the reaching dose obtaining process, the subject reaching dose is obtained (estimated) based on the feature amount and body thickness information of the subject, the radiation quality property (the spectral property of radiation), the attenuation rate of the subject, and the like, and the pixel value corresponding to the reaching dose is obtained (estimated) based on the subject reaching dose. Contents of the practical process by the dose obtaining module 306 will be described below.

The dose obtaining module 306 obtains a pixel value D corresponding to the reaching dose by executing the process of equation (1). In equation (1), D represents the pixel value (estimated value) corresponding to the reaching dose, and A represents the feature amount of the subject 15. In addition, v represents the spectral property of radiation obtained in the radiation quality information obtaining process (step S104), and L represents the body thickness information obtained in the body thickness information obtaining process (step S103). More specifically, $L_1$ represents the fat thickness obtained in the body thickness information obtaining process (step S103), and $L_2$ represents a bone thickness obtained in the body thickness information obtaining process (step S103). Furthermore, $R_1$ represents the attenuation rate of fat, $R_2$ represents the attenuation rate of bone, $R_{Air}$ represents the attenuation rate of air, and B represents a correction coefficient for correcting the influence of scattered radiation corresponding to the imaging portion and the imaging direction set by the imaging protocol (imaging information). In equation (1) below, the dose obtaining module 306 obtains a reaching dose corrected based on the correction coefficient B for correcting the influence of scattered radiation corresponding to the imaging portion and the imaging direction set by the imaging protocol (imaging information), or a pixel value corresponding to the reaching dose.

$$D = \left( \frac{A}{R_1(v, L_1) \cdot R_2(v, L_2)} \right) \cdot R_{Air}(v, L_1 + L_2) \cdot B \qquad (1)$$

In equation (1), a term ($A/(R_1 \cdot R_2)$) in which the feature amount A of the subject 15 is divided by the attenuation rate (the attenuation rate $R_1 \cdot R_2$ of the fat and bone when radiation is transmitted through the subject 15) of the subject 15 gives the pixel value (estimated value) before attenuation in the subject. The pixel value before attenuation in the subject 15 is converted into the dose, thereby obtaining the dose (subject reaching dose) of radiation having reached the subject 15. Then, the subject reaching dose ($A/(R_1 \cdot R_2)$) is multiplied by the attenuation rate $R_{Air}$ of air, thereby obtaining the reaching dose of the FPD 200. By multiplying the calculation result by the correction coefficient for correcting the influence of scattered radiation, it is possible to obtain the corrected reaching dose of the FPD 200. By converting the corrected reaching dose into a pixel value, it is possible to obtain the final pixel value D corresponding to the reaching dose.

As the feature amount A of the subject, the representative value (for example, pixel value information such as the average value, the median value, or the minimum value) of the pixel value in the subject region can be used. The feature amount A may be determined based on an exposure index (to be referred to as an "EI value" hereinafter) proportional to the irradiation dose to the FPD 200. That is, the dose obtaining module 306 can obtain the feature amount of the captured image (radiation image) based on the EI value or the pixel value of the captured image (radiation image).

A function of an attenuation rate R(v, L) represented by $R_1$, $R_2$, and $R_{Air}$ in equation (1) will be described next. The attenuation rate R(v, L) can be obtained by:

$$R(v,L) = \Sigma_{E=0}^{Emax} v(E) \cdot r(E,L) \qquad (2)$$

In equation (2), E represents a spectrum [eV] of radiation, and v(E) represents the spectral property of radiation for the spectrum E. In addition, r represents the attenuation rate of the spectrum, L represents the thickness of an object through which radiation is transmitted, and Emax represents a maximum spectrum [eV] in a table of the spectral property v. As indicated by equation (2), the attenuation rate R(v, L) can be obtained by obtaining the integral of the spectral attenuation rate r(E, L) for the spectrum E and the spectral property v(E), and totalizing the multiplication results. The total of the spectral property v(E) is normalized to be 1.

The function of the attenuation rate for the spectrum indicated by the spectral attenuation rate r(E, L) of equation (2) is given by:

$$r(E,L) = e^{-\mu(E) \cdot L} \quad (3)$$

where μ(E) represents an attenuation coefficient for the spectrum E and L represents the body thickness information.

As indicated by equation (3), for the spectral attenuation rate r(E, L) for the spectrum E, an attenuation equation when radiation is transmitted through an object, which is generally used, can be used. As the attenuation coefficient μ, an attenuation coefficient obtained by actually measuring fat, bone, and air for each object can be used, or an attenuation coefficient μ obtained by performing actual measurement using a phantom with a close attenuation property can be used. The above calculation process allows the dose obtaining module 306 to implement the reaching dose obtaining process S105.

Finally, the dose obtaining module 306 outputs, to the scattered radiation reducing module 307, the dose obtained by one of the reaching dose obtaining process (step S203) and the dose obtaining process (step S206) of the direct radiation region.

[Scattered Radiation Reducing Process: S106]

Figure 5:
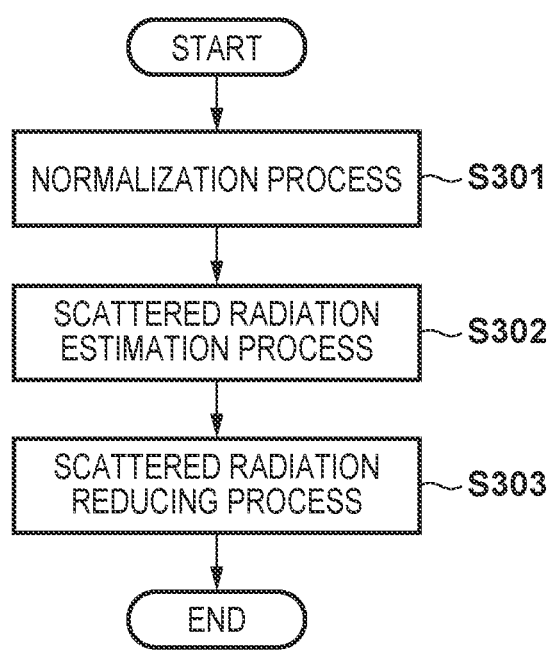
FIG. 5 is a flowchart for explaining the procedure of a scattered radiation reducing process.

The process of the scattered radiation reducing module 307 will be described as the process of the functional component of the image processing unit 300. The scattered radiation reducing module 307 performs a scattered radiation reducing process of reducing the scattered radiation of the captured image (radiation image) based on the dose information obtained in the reaching dose obtaining process (step S105). FIG. 5 is a view for explaining the procedure of the scattered radiation reducing process.

(Normalization Process: S301)

The normalization process aims at creating an image which is not influenced by a change in dose component by performing normalization with the reaching dose using the property that the scattered radiation is proportional to the irradiation dose. In step S301, the scattered radiation reducing module 307 performs a normalization process S301 of generating a normalized image by normalizing the pixel value of the captured image by the pixel value corresponding to the reaching dose obtained in the reaching dose obtaining process (step S105). The scattered radiation reducing module 307 generates a normalized image M(x, y) by performing a calculation process of dividing the pixel value of the captured image by the pixel value corresponding to the reaching dose, as given by:

$$M(x, y) = \frac{I(x, y)}{D} \quad (4)$$

In equation (4), x and y represent coordinates on the X-axis and the Y-axis, respectively, M represents the normalized image, I represents the captured image, and D represents the pixel value corresponding to the reaching dose. Note that if the dose obtaining process of the direct radiation region is executed not in step S203 but in step S206 in the process of FIG. 4A, the scattered radiation reducing module 307 generates the normalized image M(x, y) using, as D in equation (4), the pixel value corresponding to the dose of the direct radiation region.

(Scattered Radiation Estimation Process: S302)

In step S302, the scattered radiation reducing module 307 performs a scattered radiation obtaining process of creating a scattered radiation estimation image by estimating scattered radiation based on the normalized image and the reaching dose used for normalization. The scattered radiation reducing module 307 can perform the scattered radiation obtaining process using, for example, mathematical models like equations (5) to (7) below. However, the process of the scattered radiation reducing module 307 is not limited to this and various methods can be used.

$$S(x,y) = D \cdot (M(x,y) - P(x,y)) \quad (5)$$

In equation (5), x and y represent coordinates on the X-axis and the Y-axis, respectively, S(x, y) represents the pixel value of the scattered radiation estimation image, and D represents the pixel value corresponding to the reaching dose. M(x, y) presents the pixel value of the normalized image and P(x, y) represents the pixel value of a normalized primary radiation image.

The pixel value S(x, y) of the scattered radiation estimation image can be obtained by subtracting the pixel value P(x, y) of the normalized primary radiation image from the pixel value M(x, y) of the normalized image, as indicated by equation (5) to obtain a normalized scattered radiation estimation image, and multiplying the obtained normalized scattered radiation estimation image by the pixel value D corresponding to the reaching dose to perform conversion into the pixel value before normalization.

A method of deriving the pixel value P(x, y) of the normalized primary radiation image in equation (5) will be described using equation (6) below.

$$P_{n+1}(x, y) = P_n(x, y) \cdot \frac{M(x, y)}{P_n(x, y) + S_n(x, y)} \quad (6)$$

In equation (6), n represents an iteration count by a maximum likelihood method, $P_n(x, y)$ represents the pixel value of the normalized primary radiation image during iteration, M(x, y) represents the pixel value of the normalized image, and $S_n(x, y)$ represents a provisional normalized scattered radiation estimation image derived from $P_n(x, y)$.

The normalized primary radiation image P(x, y) in equation (5) represents a result of converging $P_n$ in equation (6) by iteration calculation using the maximum likelihood method. In convergence determination, a threshold may be set so as to end the iteration calculation when the difference between $P_n$ and $P_{n+1}$ becomes equal to or smaller than a predetermined value, or an iteration count for convergence at calculation accuracy may be preset and then iteration calculation may be performed by the set count. As a method of deriving $P_{n+1}(x, y)$, $P_{n+1}(x, y)$ can be obtained by multiplying $P_n(x, y)$ before iteration by a division result of dividing M(x, y) by the sum $(P_n + S_n)$ of $P_n$ and $S_n$. The division result of dividing M(x, y) by the sum $(P_n + S_n)$ of $P_n$ and $S_n$ is in a form in which the normalized image M obtained by normalizing the captured image is the sum of the normalized primary radiation image P and the normalized scattered radiation image S, and converges to 1 by iteration using the maximum likelihood method. As an example of the initial value of $P_n(x, y)$, for example, 0.5 or the like may be set evenly, or the value of M(x, y) may be given.

An example of a method of deriving the provisional normalized scattered radiation estimation image $S_n(x, y)$ in equation (6) will be described using equation (7) below.

$$S_n(x,y) = W_A \cdot (-P_n(t_x, t_y) \log_e P_n(t_x, t_y))^* e^{-W_B((x-t_x)^2 + (y-t_y)^2)} + W_C \quad (7)$$

where x and $t_x$ represent coordinates on the X-axis, y and $t_y$ represent coordinates on the Y-axis, and $W_A$, $W_B$, and $W_C$ represent parameters.

The provisional normalized scattered radiation estimation image $S_n(x, y)$ in equation (6) can be derived from the sum of the term of $W_C$ and the term of the convolution integral of a factor formed from $P_n$ and a factor of an exponential function of a Napier's constant e, as indicated by equation (7). The factor "$-P_n(t_x, t_y)\log_e P_n(t_x, t_y)$" formed from $P_n$ approximates a function of the intensity of scattered radiation generated at the coordinates $(t_x, t_y)$. The factor of the exponential function of the Napier's constant e approximates the spread function of scattered radiation. The convolution integral of the factor formed from $P_n$ and the factor of the exponential function of the Napier's constant e indicates that scattered radiation at the x and y coordinates is calculated from the sum of scattered radiation generated from the coordinates $(t_x, t_y)$ as a peripheral pixel. The term of $W_C$ of a DC component indicates an offset component included in the image.

The parameters $W_A$, $W_B$, and $W_C$ can be derived by substituting equation (7) into the scattered radiation estimation image and the primary radiation image for the subject 15 and performing fitting by a nonlinear least square method. As the primary radiation image, an image can be obtained by irradiating the FPD 200 in a raster scan form with radiation narrowed within a minimal range on the subject 15 so no scattered radiation is generated, and as the scattered radiation estimation image, an image can be obtained by excluding the primary radiation image from the captured image obtained by irradiating the overall FPD 200.

(Scattered Radiation Reducing Process: S303)

In step S303, the scattered radiation reducing module 307 executes a scattered radiation reducing process of subtracting (reducing) the scattered radiation component included in the captured image (step S102) based on the scattered radiation estimation image obtained in the scattered radiation estimation process (step S302). As a practical example, based on a formula like equation (8) below, the scattered radiation reducing module 307 can obtain a scattered radiation reduction image with reduced scattered radiation.

$$O(x,y) = I(x,y) - K \cdot S(x,y) \quad (8)$$

In equation (8), x and y represent coordinates on the X-axis and Y-axis in the image, respectively, O(x, y) represents the pixel value of the scattered radiation reduction image, and I(x, y) represents the pixel value of the captured image. Furthermore, K represents a scattered radiation reduction rate, and S(x, y) represents the pixel value of the scattered radiation estimation image.

As indicated by equation (8), the scattered radiation reduction image can be obtained by subtracting, from the pixel value I(x, y) of the captured image, the multiplication result of multiplying the pixel value S(x, y) of the scattered radiation estimation image by the scattered radiation reduction rate K. The scattered radiation reduction rate K has a value settable within the range of 0 to 1. The scattered radiation reduction rate K may be set by the user from the operation unit 500, or a value preset for each imaging technique can be used as the scattered radiation reduction rate K.

The scattered radiation reducing module 307 can send the obtained scattered radiation reduction image to the display unit 400 via the I/O unit 301 (input/output unit), and the CPU 309 (control unit) can execute display control for displaying the scattered radiation reduction image on the display unit 400. The scattered radiation reducing module 307 can perform, for the scattered radiation reduction image, an image process such as a tone process and a frequency enhancement process before sending the scattered radiation reduction image to the I/O unit 301, thereby adjusting the image to an image easy for the user to see.

In the conventional technique, if the pixel value in the direct radiation region is saturated or if there is no direct radiation region, it is impossible to estimate a reaching dose. However, as described above, according to this embodiment, even in such case, it is possible to obtain the reaching dose of radiation that reaches the FPD 200 from a radiation image captured without using information (for example, in the NDD method of the conventional technique, a tube current, an irradiation time, and SID information are required) that readily changes for each imaging operation, and information obtained in advance in the image processing apparatus. Based on the obtained reaching dose information, it is possible to perform the scattered radiation estimation process, and obtain a scattered radiation reduction image by subtracting a scattered radiation component included in the captured image.

The embodiment of the present invention has been described above. However, the present invention is not limited to the embodiment, as a matter of course, and various changes and modifications can be made within the spirit and scope of the present invention. The practical formula in the scattered radiation estimation process is merely an example, and the present invention is not limited to this.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-231546, filed Dec. 11, 2018 which is hereby incorporated by reference herein in its entirety.

What is claimed is:

1. An image processing apparatus for processing a radiation image output from a radiation detection unit including a plurality of pixels, comprising:
   an imaging protocol obtaining unit configured to obtain an imaging protocol for imaging a subject; and
   a dose obtaining unit configured to obtain, in a case where it is determined that there is a direct radiation region in the radiation image, dose information of radiation using at least one of pixel values of the direct radiation region in the radiation image, and to estimate, in a case where it is determined that there is no direct radiation region in the radiation image, dose information of radiation using at least one of pixel values of the radiation image and information obtained based on the imaging protocol,
   wherein the direct radiation region is a region where radiation reaches the radiation detecting unit without passing through the subject.

2. The apparatus according to claim 1, wherein the information obtained from the imaging protocol comprises body thickness information of the subject and radiation quality information of the radiation.

3. The apparatus according to claim 1, wherein the dose obtaining unit obtains, as the dose information, one of a reaching dose of radiation having reached the radiation detection unit and a pixel value corresponding to the reaching dose.

4. The apparatus according to claim 1, further comprising a body thickness information obtaining unit configured to obtain body thickness information of the subject based on the imaging protocol.

5. The apparatus according to claim 4, wherein the body thickness information obtaining unit obtains the body thickness information corresponding to one of an imaging portion and an imaging direction of the subject included in the imaging protocol.

6. The apparatus according to claim 4, further comprising a storage unit configured to store a body thickness information table for associating the imaging protocol and the body thickness information with each other.

7. The apparatus according to claim 6, wherein the body thickness information obtaining unit specifies an imaging portion and an imaging direction included in the imaging protocol, and obtains body thickness information corresponding to the specified imaging portion and the imaging direction with reference to the body thickness information table.

8. The apparatus according to claim 1, further comprising a radiation quality information obtaining unit configured to obtain radiation quality information of the radiation based on the imaging protocol.

9. The apparatus according to claim 8, wherein based on one of a tube voltage and a filter type included in the imaging protocol, the radiation quality information obtaining unit obtains, as the radiation quality information of the radiation, information of a spectral property of the radiation obtained from a preset spectral property table.

10. The apparatus according to claim 1, wherein the dose obtaining unit performs a region determination process of determining, based on a pixel value of the radiation image, the direct radiation region where radiation directly reaches the radiation detection unit from a radiation generation unit.

11. The apparatus according to claim 1, wherein the dose obtaining unit compares a reference value of a saturated pixel value with a pixel value in the direct radiation region, determines, in a case where the pixel value in the direct radiation region is not smaller than the reference value, that the pixel value in the direct radiation region is saturated, and determines, in a case where the pixel value in the direct radiation region is smaller than the reference value, that the pixel value in the direct radiation region is not saturated.

12. The apparatus according to claim 1, wherein in a case where it is determined that there is the direct radiation region in the radiation image, and in a case where it is determined that the at least one of pixel values of the direct radiation region is not saturated, the dose obtaining unit obtains, as the dose information, one of a reaching dose of radiation having reached the radiation detection unit and a pixel value corresponding to the reaching dose using information obtained by performing a statistical process of the at least one of pixel values of the radiation image.

13. The apparatus according to claim 1, wherein in a case where it is determined that there is the direct radiation region in the radiation image and in a case where it is determined that the at least one of pixel values of the direct radiation region is saturated, the dose obtaining unit estimates, as the dose information, one of a reaching dose of radiation having reached the radiation detection unit and a pixel value corresponding to the reaching dose using the at least one of pixel values of the radiation image and an attenuation property obtained based on the imaging protocol.

14. The apparatus according to claim 13, wherein the dose obtaining unit obtains, as the attenuation property, an attenuation rate of the subject and an attenuation rate of air based on body thickness information and radiation quality information, both of which have been obtained based on the imaging protocol.

15. The apparatus according to claim 13, wherein the dose obtaining unit obtains the at least one of pixel values of the radiation image based on an EI value.

16. The apparatus according to claim 13, wherein the dose obtaining unit obtains one of a reaching dose corrected based on a correction coefficient for correcting an influence of scattered radiation corresponding to an imaging portion and an imaging direction set by the imaging protocol, and a pixel value corresponding to the reaching dose.

17. The apparatus according to claim 1, further comprising a scattered radiation reducing unit configured to perform a scattered radiation reducing process of reducing scattered radiation of the radiation image based on the dose information obtained by the dose obtaining unit.

18. An image processing method of processing a radiation image output from a radiation detection unit including a plurality of pixels, comprising:
   obtaining an imaging protocol for imaging a subject; and
   obtaining, in a case where it is determined that there is a direct radiation region in the radiation image, dose information of radiation using at least one of pixel values of the direct radiation region in the radiation image, and estimating, in a case where it is determined that there is no direct radiation region in the radiation image, dose information of radiation using at least one of pixel values of the radiation image and information obtained based on the imaging protocol, wherein the direct radiation region is a region where radiation reaches the radiation detecting unit without passing through the subject.

19. A computer-readable storage medium storing a program that when executed on a computer causes the computer to perform the method defined in claim 18.

* * * * *